United States Patent [19]

Godfrey, Jr. et al.

[11] Patent Number: 5,773,614

[45] Date of Patent: Jun. 30, 1998

[54] PROCESS FOR THE PREPARATION OF AN ANTIVIRAL AGENT

[75] Inventors: Jollie D. Godfrey, Jr., Trenton; Richard H. Mueller, Ringoes, both of N.J.

[73] Assignee: Bristol-Myers Squibb Co., Princeton, N.J.

[21] Appl. No.: 713,333

[22] Filed: Sep. 13, 1996

Related U.S. Application Data

[63] Continuation-in-part of Ser. No. 416,403, Apr. 3, 1995, abandoned.

[51] Int. Cl.$^6$ .................. C07D 473/18; C07D 473/40; C07C 69/78; C07C 49/753
[52] U.S. Cl. .................. 544/276; 544/277; 556/436; 560/106; 560/123; 549/342; 568/329
[58] Field of Search .................. 544/276; 568/329; 556/436; 560/106

[56] References Cited

U.S. PATENT DOCUMENTS

| | | | |
|---|---|---|---|
| 5,064,961 | 11/1991 | Bisacchi et al. | 544/276 |
| 5,126,345 | 6/1992 | Slusarchyk et al. | 514/254 |
| 5,153,352 | 10/1992 | Norbeck et al. | 560/17 |
| 5,185,463 | 2/1993 | Godfrey et al. | 562/506 |
| 5,233,076 | 8/1993 | Ahmad | 560/106 |
| 5,235,052 | 8/1993 | Pariza et al. | 544/276 |
| 5,412,134 | 5/1995 | Singh et al. | 556/437 |
| 5,608,064 | 3/1997 | Singh et al. | 544/277 |

FOREIGN PATENT DOCUMENTS

| | | |
|---|---|---|
| 322854 | 7/1989 | European Pat. Off. . |
| 358154 | 3/1990 | European Pat. Off. . |
| 444597 | 9/1991 | European Pat. Off. . |
| 452729 | 10/1991 | European Pat. Off. . |
| 458363 | 11/1991 | European Pat. Off. . |
| 484843 | 5/1992 | European Pat. Off. . |
| 572209 | 12/1993 | European Pat. Off. . |
| 579421 | 1/1994 | European Pat. Off. . |

OTHER PUBLICATIONS

W. von E. Doering et al., Tetrahedron, vol. 26, pp. 2825–2835, 1970.
Salaun et al., Tetrahedron, vol. 30, pp. 1413–1421, 1974.
Hsiao et al., Tetrahedron Letters, vol. 31, pp. 6609–6612, 1990.
Sugimara et al., Chemical Abstracts, vol. 121, No. 13, p. 980, abstract No. 157191c, 1994.
Ichikawa et al., Chemical Abstracts, vol. 119, No. 13, pp. 721–722, abstract No. 137552b, 1993.
Kang, J.A.C.S. 112, 3252 (1990).

Primary Examiner—Mark L. Berch
Attorney, Agent, or Firm—Stephen B. Davis

[57] ABSTRACT

(1R,trans) Diprotected 3-methylene-1,2-cyclopropanedimethanol is oxidized to an optically active diol

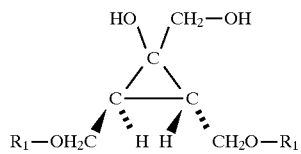

which is then cyclized to an orthoester

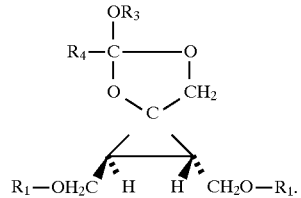

This orthoester is then treated with a Lewis acid catalyst to give the cyclobutanone

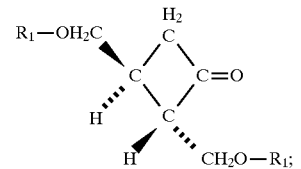

which is useful as an intermediate in the preparation of the antiviral agent [1R-(1α,2β,3α)]-2-amino-9-[2,3-bis(hydroxymethyl)cyclobutyl]-1,9-dihydro-6H-purin-6-one.

8 Claims, No Drawings

PROCESS FOR THE PREPARATION OF AN ANTIVIRAL AGENT

This application is a continuation-in-part of Ser. No. 416,403 filed Apr. 3, 1995, now abandoned.

BACKGROUND OF THE INVENTION

The compound [1R-(1α,2β,3α)]-2-amino-9-[2,3-bis(hydroxymethyl)cyclobutyl]-1,9-dihydro-6H-purin-6-one, i.e.

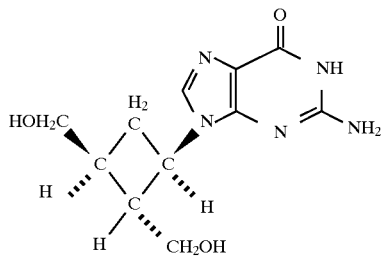

is an antiviral agent with activity against human cytomegalovirus, herpes simplex virus type 1 and 2, varicella zoster virus, and hepatitis B.

Norbeck et al. in U.S. Pat. No. 5,153,352 disclose the preparation of this and related pyrinyl and pyrimidinyl antiviral agents by several routes. One disclosed process utilizes the conversion of the optically pure compound of the formula

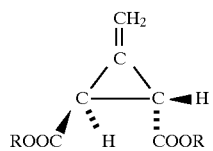

wherein R is an alkyl of 1 to 4 carbons as the starting material. Norbeck et al. obtain this starting material by resolving racemic Feist's acid with quinine according to known procedures, e.g. Doering et al., Tetrahedron, Vol. 26, p. 2825–2835 (1970).

Godfrey et al. in U.S. Pat. No. 5,185,463 disclose an improved process for resolving Feist's acid.

Hsiao et al., Tetrahedron Letters, Vol. 31, p. 6609–6612 (1990), disclose the preparation of protected forms of (2S, 3S)-2,3-bis(hydroxymethyl) cyclobutanone from Feist's acid.

Bisacchi et al. in U.S. Pat. No. 5,064,961 disclose preparing the antiviral agent [1R-(1α,2β,3α)]-2-amino-9-[2,3-bis(hydroxymethyl)cyclobutyl]-1,9-dihydro-6H-purine-6-one from the optically active intermediate

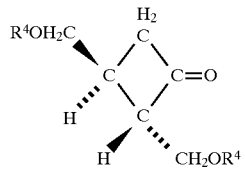

wherein $R^4$ is a protecting group such as benzoyl.

Other procedures for preparing this optically active protected cyclobutanone are disclosed by Ahmad in U.S. Pat. No. 5,233,076 and Pariza et al. in U.S. Pat. No. 5,235,052.

Singh et al. in U.S. Pat. No. 5,412,134 disclose additional process for converting this optically active protected cyclobutanone to the optically active diprotected 2,3-hydroxymethyl cyclobutanol which can then be converted to the desired antiviral agent.

Singh et al. in European Patent Application 579,421 and U.S. Ser. No. 007,950 filed Jan. 25, 1993 disclose an improved process for converting the optically active diprotected 2,3-hydroxymethylcyclobutanol to the desired antiviral agent [1R-(1α,2β,3α)]-2-amino-9-[2,3-bis(hydroxymethyl)cyclobutyl]-1,9-dihydro-6H-purine-6-one.

BRIEF SUMMARY OF THE INVENTION

This invention is directed to an improved process for converting the optically active compound of the formula

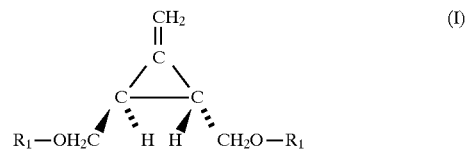

to the optically active cyclobutanone of the formula IV

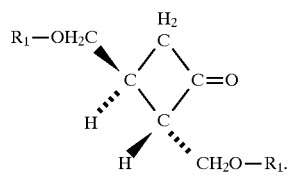

In the first step of the process of this invention, the 3-methylene starting material of formula I is oxidized to the diol of the formula (II)

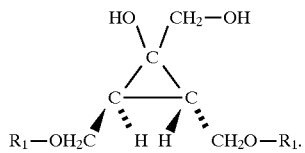

A suitable oxidizing reagent for this reaction is osmium tetroxide.

In the next step of the process of this invention, the diol of formula II is converted to the cyclic orthoester of the formula (III)

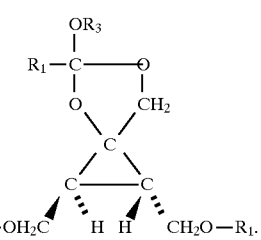

This conversion is performed by treating the diol of formula II with a trimethyl or triethyl orthoester in the presence of a weak acid catalyst.

The cyclic orthoester of formula III is then converted to the optically active cyclobutanone of formula IV by treating with a Lewis acid catalyst.

$R_1$ in the above formulas is a hydroxy protecting group. Suitable hydroxy protecting groups include silyl groups such as t-butyldimethylsilyl, t-butyldiphenylsilyl, (triphenylmethyl)dimethylsilyl, methyldiisopropylsilyl, and triisopropylsilyl, benzyl and substituted benzyl grous such as p-methoxybenzyl, triphenylmethyl and substituted triphenylmethyl groups such as 4-methoxy substituted triphenylmethyl and 4,4-dimethylsubstituted triphenylmethyl, and acyl groups of the formula

wherein $R_2$ is straight or branched chain alkyl of 1 to 6 carbons or phenyl.

$R_3$ is methyl or ethyl.

$R_4$ is straight or branched chain alkyl of 1 to 6 carbons or phenyl.

This invention is also directed to the novel intermediates of formulas II and III shown above.

DETAILED DESCRIPTION OF THE INVENTION

According to the process of this invention a solution of the diprotected resolved compound of formula I in an organic solvent is treated with a oxidizing agent to give the diol of formula II. The preferred oxidizing agent is osmium tetroxide employed in an aqueous solution. Suitable organic solvents for the diprotected resolved compound of formula I include acetone, which is preferred, ethyl acetate, dichloromethane, etc.

In a preferred embodiment of this invention the osmium tetroxide is employed in catalytic amounts by including a cooxidant in the reaction mixture to regenerate the spent osmium tetroxide. 4-Methylmorpholine N-oxide is the preferred cooxidant. When the cooxidant is employed, the osmium tetroxide is utilized in an aqueous solution containing from about 0.2 mole percent to about 0.8 mole percent, preferably about 0.5 mole percent.

The reaction of diprotected resolved compound of formula I to the diol of formula II is performed at room temperature.

In the next step of the process of this invention, the diol of formula II is converted to the spiro compound of formula III. A solution of the diol of formula II in an organic solvent such toluene, which is preferred, benzene, etc., is treated with a trimethyl or triethyl orthoester of the formula

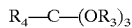

such as trimethyl orthoacetate, which is preferred, trimethyl orthobenzoate, trimethyl orthobutyrate, triethyl orthoacetate, triethyl orthopropionate, trimethyl orthovalerate, etc. Preferably, the reaction is performed in the presence of an acid catalyst such as pyridium p-toluenesulfonate, which is preferred, or other well known acid catalysts including camphorsulfonic acid, methanesulfonic acid, p-toluenesulfonic acid, anhydrous hydrochloric acid, a polymeric resin containing a sulfonic acid group, e.g. Dowex®-50 acid form, and acidic clays such as montmorillonite K 10.

The reaction of the diol of formula II to the spiro compound of formula III is performed at room temperature preferably under an inert atmosphere.

In the next step of the process of this invention, the spiro compound of formula III is converted to the optically active diprotected cyclobutanone of formula IV. A solution of the spiro compound of formula III in an organic solvent such as toluene, ethylacetate, or dichloromethane, which is preferred, is treated with a Lewis acid catalyst.

Suitable Lewis acid catalysts for this reaction include boron trifluoride etherate, which is preferred, trimethylsilyl trifluoromethanesulfonate, boron trichloride, boron tribromide, diethylaluminum chloride, ethylaluminum dichloride, aluminum trichloride, titanium tetrachloride, tin tetrachloride, etc.

The reaction of the spiro compound of formula III and the Lewis acid catalyst is performed at low temperatures, preferably at about 0° C. The spiro compound of formula III can be utilized in crude form. The resulting diprotected optically active cyclobutanone product of formula IV is purified by conventional techniques following completion of the reaction.

The diprotected dimethanol compound of formula I is prepared by treating (1R-trans)-3-methylene-1,2-cyclopropanedimethanol with a protecting agent such as a chloride of the formula $$R_1\text{—Cl} \qquad (V)$$

when $R_1$ is benzyl, substituted benzyl, triphenylmethyl, substituted triphenylmethyl, a hindered silyl, or an acyl group of the formula (VI)

or by treating with an anhydride of the formula (VII)

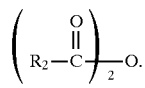

The preferred $R_1$ protecting group in the compound of formula I is benzoyl which is prepared by reacting (1R-trans)-3-methylene-1,2-cyclopropanedimethanol with benzoic anhydride as described in Example 1(c) of U.S. Pat. No. 5,185,463.

The optically active cyclobutanone of formula IV can be converted to the antiviral agent [1R-(1α,2β,3α)]-2-amino-9-[2,3-bis(hydroxymethyl)cyclobutyl]-1,9-dihydro-6H-purin-6-one by known methods.

As taught by Bisacchi et al. in U.S. Pat. No. 5,064,961 and Singh et al. in European Patent Application 572,209, the optically active cyclobutanone of formula IV can be treated with a reducing agent to give the optically active cyclobutanol of the formula (VIII)

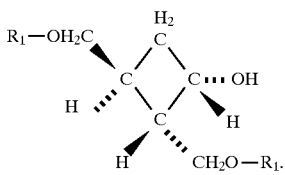

Suitable reducing reagents include hydride reagents such as lithium tri-sec-butylborohydride, lithium trisiamylborohydride, diisobutylaluminum hydride and the like, hindered borane reducing agents such as dicyclohexylborane, disiamylborane, and the like, dialkylaluminum chlorides such as diisobutylaluminum chloride, alkylaluminum dichlorides such as isobutylaluminum dichloride, trialkylaluminum compounds such as triisolbutylaluminum and iridium tetrachloride in the presence of phosphorous acid.

The optically active cyclobutanol of formula VIII is then converted to the optically active compound of the formula (IX)

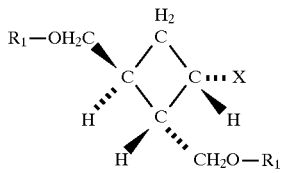

wherein X is a leaving group such as chloro, bromo, iodo, an aryl sulfonyloxy group such as p-toluenesulfonyloxy, an alkyl sulfonyloxy group such as methanesulfonyloxy, a substituted alkyl sulfonyloxy group, preferably a perfluoroalkanesulfonyloxy group such as trifluoromethanesulfonyloxy, a nitro substituted aryl sulfonyloxy group such as p-nitrobenzenesulfonyloxy, or fluorosulfonyloxy as taught by Bisacchi et al. in U.S. Pat. No. 5,064,961 and European Patent Application 579,421. For example, when X is a perfluoroalkane sulfonyloxy group, the cyclobutanol of formula VIII is treated with the perfluoroalkanesulfonic anhydride such as trifluoromethanesulfonic anhydride in an inert solvent such as dichloromethane in the presence of a base such as pyridine. When X is a nitro-substituted aryl sulfonyloxy group as p-nitrobenzenesulfonyloxy, the cyclobutanol of formula VIII is reacted with a nitro-substituted aryl sulfonylating reagent such as p-nitrobenzenesulfonyl chloride in pyridine or in an inert solvent such as dichloromethane or chloroform containing a base such as pyridine or triethylamine. When X is fluorosulfonyloxy, the cyclobutanol of formula VIII is reacted with fluorosulfonic anhydride in pyridine or in an inert solvent such as dichloromethane or chloroform containing a base such as pyridine or triethylamine.

The optically active compound of formula IX can then be treated with a protected guanine such as 2-amino-6-benzyloxypurine, 2-amino-6-methoxyethoxypurine, 2-amino-6-chloropurine as taught by Bisacchi et al. in U.S. Pat. No. 5,064,961 to give the optically active compound of the formula (X)

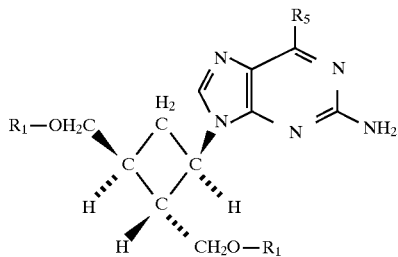

wherein $R_5$ is a group which can be converted into a 6-oxo-substituent such as a protected hydroxy or a chloro. Removal of the $R_1$ protecting groups and conversion of $R_5$ to a 6-oxo gives the desired antiviral agent [1R-(1α,2β,3α)]-2-amino-9-[2,3-bis(hydroxymethyl)cyclobutyl]-1,9-dihydro-6H-purin-6-one. In the preferred embodiment of U.S. Pat. No. 5,064,961, Example 1, the $R_1$ groups are benzoyl and $R_3$ is benzyloxy and the intermediate of formula X is treated with a solution of sodium methoxide in methanol to remove the $R_1$ benzoyl groups and then treated with hydrochloric acid in aqueous methanol to remove the 6-benzyl protecting group and give the desired product.

An alternate procedure for converting the optically active intermediate of formula IX to the desired antiviral agent is taught by Singh et al. in European Patent Application 579,421. In this procedure, the intermediate of formula IX is treated with a purine salt of the formula (XI)

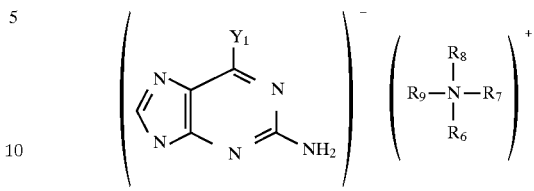

wherein $Y_1$ is iodo, bromo or chloro and $R_6$, $R_7$, $R_8$ and $R_9$ are independently straight or branched chain alkyl of 1 to 10 carbons or substituted alkyl of 1 to 10 carbons wherein said substituent is selected from alkoxy of 1 to 6 carbons and aryl, to give the optically active compound of the formula (XII)

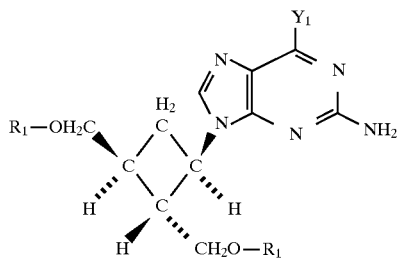

Removal of the $R_1$ protecting groups and conversion of $Y_1$ to a 6-oxo yields the desired antiviral agent [1R-(1α,2β,3α)]-2-amino-9-[2,3-bis(hydroxymethyl)cyclobutyl]-1,9-dihydro-6H-purin-6-one. In the preferred embodiment of European Patent Application 579,421, the purine salt of formula XI is 6-iodo-9H-purin-2-amine, ion (1-), triethyl (phenylmethyl)ammonium (1:1) salt or 6-iodo-9H-purin-2-amine, ion (1-), tetrabutylammonium (1:1) salt, $R_1$ is benzoyl, and the intermediate of formula XII is treated with a solution of sodium methoxide in methanol to remove the $R_1$ protecting groups and convert the 6-iodo to a 6-methoxy followed by treatment with hydrochloric acid to convert the 6-methoxy to a 6-oxo.

The following example is illustrative of the invention.

EXAMPLE 1

(2S-trans)-2,3-Bis[(benzoyloxy)methyl] cyclobutanone a) (1S-trans)-3-Hydroxy-1,2,3-cyclopropanetrimethanol, $\alpha^1$, $\alpha^2$-dibenzoate Water (9.6 ml) was added to a solution of (1R-trans)-3-methylene-1,2-cyclopropanedimethanol, dibenzoate in acetone (80 ml) at room temperature under an argon atmosphere. To the resulting solution was added a 60 weight percent aqueous solution of 4-methylmorpholine N-oxide (8.1 ml, about 9.15 g. of solution containing about 5.49 g of 4-methylmorpholine N-oxide, 46.87 mmole) followed by a 4% aqueous solution osmium tetroxide (0.98 ml, about 0.154 mmole, 0.005 eq., 0.5 mole %). The resulting mixture was stirred at room temperature under argon in the dark. The reaction was monitored by TLC analysis. After stirring at room temperature for 22 hours, water (15 ml) was added, followed by sodium metabisulfite (8.0 g, 42.08 mmole). After stirring for about 10 minutes, magnesium silicate (6 g) was added. After stirring for about 15 minutes, the resulting mixture was filtered through a bed of magnesium silicate (18 g) and the filter bed was thoroughly washed with acetone and ethyl acetate. The filtrate was partially concentrated and additional ethyl acetate was added (final volume about 400 ml). The resulting solution was washed with water: 1N hydrochloric acid (5:2, 70 ml), 1N hydrochloric acid (3×50 ml), 1N sodium bicarbonate (50 ml) and brine. After drying over magnesium sulfate, the solvent was removed at reduced pressure to give the desired product as a pale yellow solid which was dried under vacuum (11.05 g).

b) (1S,2S)-5-Methoxy-5-methyl-4,6-dioxaspiro-[2.4] heptane-1,2-dimethanol, dibenzoate To a suspension of the product from part (a) (1.07 g, 3.0 mmole) in anhydrous toluene (10 ml) at room temperature under argon was added trimethyl orthoacetate (0.57 ml, 4.5 mmole, 1.5 eq.) and pyridinium p-toluenesulfonate (11.5 mg, 0.046 mmole, 1.52 mole %). The resulting suspension was stirred at room temperature for 70 minutes, a clear solution was obtained after about 30 minutes. The resulting mixture was concentrated at reduced pressure to give crude (1S,2S)-5-methoxy-5-methyl-4,6-dioxaspiro-[2.4]heptane-1,2-dimethanol, dibenzoate as a nearly colorless oil.

c) (2S-trans)-2,3-Bis[(benzoyloxy)methyl] cyclobutanone

The crude product from part (b) was dissolved in anhydrous dichloromethane (10 ml). After cooling to about 0° C. (ice bath), boron trifluoride etherate (40 μl, 0.325 mmol, 0.108 eq.) was added. After stirring at about 0° C. for one hour, the reaction mixture was diluted with ethyl acetate. The resulting solution was washed with 1N hydrochloric acid, 1N sodium bicarbonate, and brine. After drying over magnesium sulfate, the solvent was removed at reduced pressure to give 960 mg of crude product as a colorless solid.

This crude product was dissolved with heating in 2-propanol (5 ml). After cooling to room temperature, the mixture was placed in a refrigerator (about 4° C.). After standing in the cold for 4 hours, ice cold 2-propanol (5 ml) was added so as to obtain a pourable mixture. The product was collected by filtration, washed with ice cold 2-propanol, and dried under vacuum to give 890 mg of pure (2S-trans)-2,3-bis[(benzoyloxy)methyl]cyclobutanone as a colorless, fluffly solid. TLC (silica gel, ethyl ether:hexane (6:4) $R_f$=0.32; (silica gel, toluene:ethyl ether, 84:16) $R_f$=0.41.

What is claimed is:

1. A process for preparing the optically active cyclobutanone of the formula

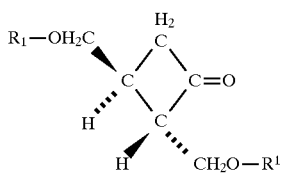

wherein $R_1$ is a hydroxy protecting group which comprises:

a) oxidizing the optically active 3-methylene compound of the formula

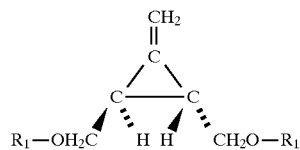

with osmium tetroxide to give the optically active diol of the formula

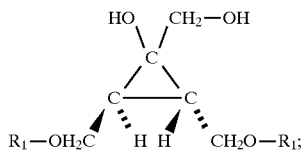

b) converting the diol product from step (a) to the cyclic orthoester of the formula

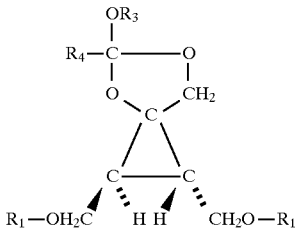

by treating the product from step (a) with a trimethyl or triethyl orthoester of the formula

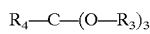

in the presence of an acid catalyst wherein $R_3$ is methyl or ethyl and $R_4$ is straight or branched chain alkyl of 1 to 6 carbons or phenyl; and c) treating the cyclic orthoester product from step (b) with a Lewis acid catalyst to give the desired optically active cyclobutanone.

2. The process of claim 1 wherein the osmium tetroxide in step (a) is employed in catalytic amounts by including 4-methylmorpholine, N-oxide as a cooxidant.

3. The process of claim 1 wherein the trimethyl or triethyl orthoester in step (b) is trimethyl orthoacetate and the acid catalyst is step (b) is pyridium p-toluenesulfonate.

4. The process of claim 1 wherein the Lewis acid catalyst in step (c) is boron trifluoride etherate, trimethylsilyl trifluoromethanesulfonate, boron trichloride, boron tribromide, diethylaluminum chloride, ethylaluminum dichloride, aluminum trichloride, titanium tetrachloride, or tin tetrachloride.

5. The process of claim 4 wherein the Lewis acid catalyst in step (c) is boron trifluoride etherate.

6. A process for preparing the optically active cyclobutanone of the formula

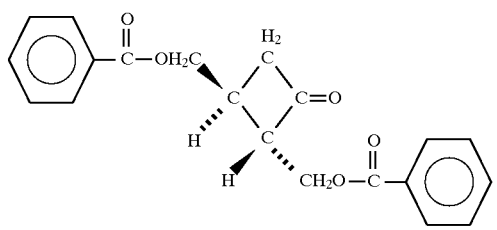

which comprises:

a) oxidizing the optically active 3-methylene compound of the formula

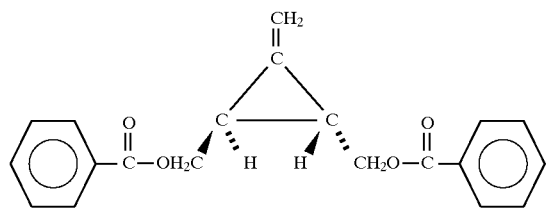

with an aqueous solution containing a catalytic amount of osmium tetroxide and 4-methylmorpholine N-oxide as cooxidant to give the optically active diol of the formula

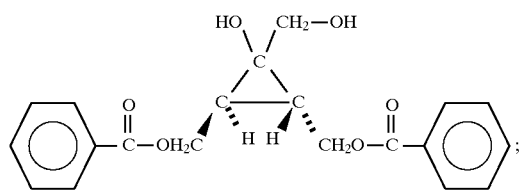

b) converting the diol product from step (a) to the cyclic orthoester of the formula

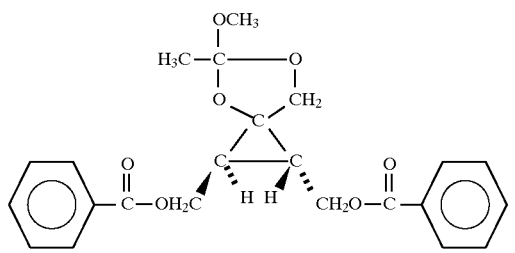

by treating the product from step (a) with trimethyl orthoacetate in the presence of pyridium p-toluenesulfonate; and c) treating the cyclic orthoester product from step (b) with boron trifluoride etherate to give the desired optically active cyclobutanone.

7. A process for preparing the antiviral agent [1R-(1α,2β,3α)]-2-amino-9-[2,3-bis(hydroxymethyl)cyclobutyl]-1,9-dihydro-6H-purine-6-one which comprises:

a) oxidizing the optically active 3-methylene (1R-trans) compound of the formula

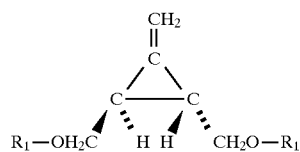

wherein $R_1$ is a hydroxy protecting group with osmium tetroxide to give the optically active diol of the formula

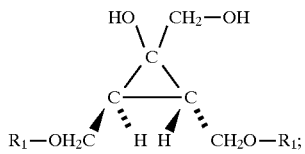

b) converting the diol product from step (a) to the cyclic orthoester of the formula

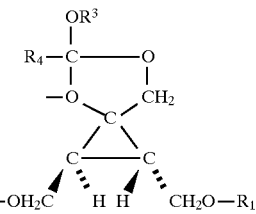

by treating the product from step (a) with a trimethyl or triethyl orthoester of the formula

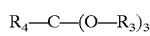

in the presence of an acid catalyst wherein $R_3$ is methyl or ethyl and $R_4$ is straight or branched chain alkyl or 1 to 6 carbons or phenyl;

c) treating the cyclic orthoester product from step (b) with a Lewis acid catalyst to give the optically active cyclobutanone of the formula

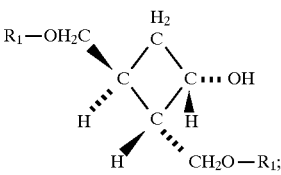

d) treating the optically active cyclobutanone product from step (c) with a reducing agent to give the optically active cyclobutanol of the formula

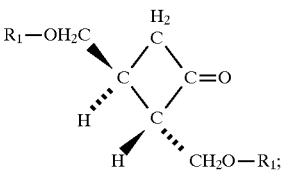

e) treating the optically active cyclobutanol product from step (d) with a sulfonylating reagent to give the optically active cyclobutane compound of the formula

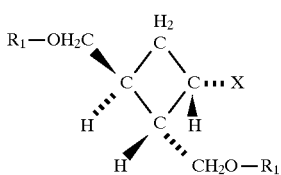

wherein X is a leaving group selected from the group consisting of p-toluenesulfonyloxy, methanesulfonyloxy, trifluoromethanesulfonyloxy, p-nitrobenzenesulfonyloxy, and fluorosulfonyloxy;

f) reacting the product from step (e) with the purine of the formula

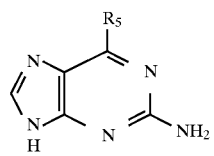

to give the optically active compound of the formula

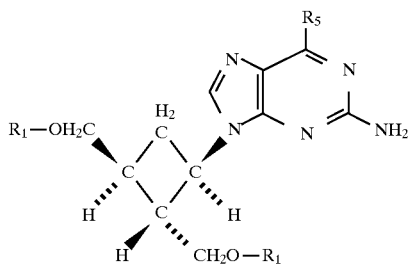

wherein $R_5$ is a protected hydroxy or chloro group; and g) treating the product step (f) to remove the $R_1$ hydroxy protecting groups and to convert the $R_5$ group to a 6-oxo.

8. A process for preparing the antiviral agent [1R-(1α,2β, 3α)]-2-amino-9-[2,3-bis(hydroxymethyl)cyclobutyl]-1,9-dihydro-6H-purin-6-one which comprises:

a) oxidizing the optically active 3-methylene (1R-trans) compound of the formula

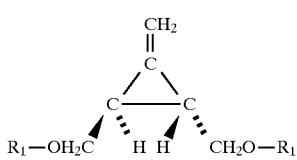

wherein $R_1$ is a hydroxy protecting group with osmium tetroxide to give the optically active diol of the formula

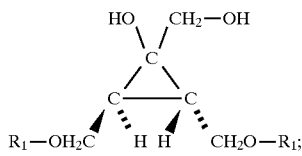

b) converting the diol product from step (a) to the cyclic orthoester of the formula

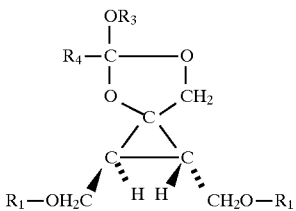

by treating the product from step (a) with a trimethyl or triethyl orthoester of the formula

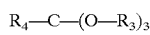

$$R_4-C-(O-R_3)_3$$

in the presence of an acid catalyst wherein $R_3$ is methyl or ethyl and $R_4$ is straight or branched chain alkyl of 1 to 6 carbons or phenyl;

c) treating the cyclic orthoester product from step (b) with a Lewis acid catalyst to give the optically active cyclobutanone of the formula

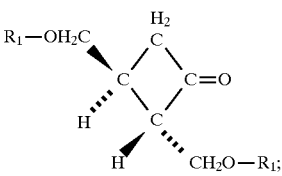

d) treating the optically active cyclobutanone product from step (c) with a reducing agent to give the optically active cyclobutanol of the formula

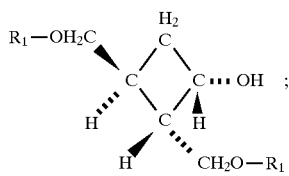

e) treating the optically active cyclobutanol product from step (d) with a sulfonylating reagent to give the optically active cyclobutane compound of the formula

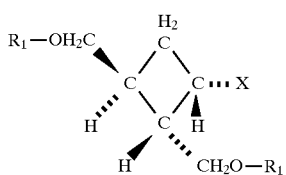

wherein X is a leaving group selected from the group consisting of p-toluenesulfonyloxy, methanesulfonyloxy, trifluoromethanesulfonyloxy, p-nitrobenzenesulfonyloxy, and fluorosulfonyloxy;

f) reacting the product from step (e) with the purine salt of the formula

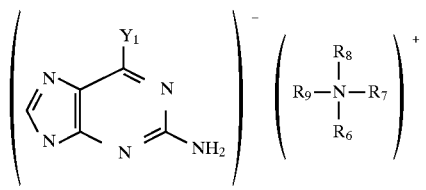

wherein $Y_1$ is iodo, bromo or chloro and $R_6$, $R_7$, $R_8$ and $R_9$ are independently selected from the group consisting of straight or branched chain alkyl of 1 to 10 carbons or substituted alkyl of 1 to 10 carbons wherein said substituent is alkoxy of 1 to 6 carbons or aryl, to give the optically active compound of the formula

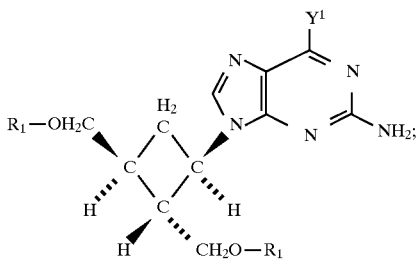

and g) treating the product step (f) to remove the $R_1$ hydroxy protecting groups and to convert the $Y_1$ group to a 6-oxo.

* * * * *